(12) United States Patent
Atanasoska et al.

(10) Patent No.: US 8,277,833 B2
(45) Date of Patent: Oct. 2, 2012

(54) MEDICAL DEVICES HAVING SURFACE COATINGS

(75) Inventors: Liliana Atanasoska, Edina, MN (US); James Lee Shippy, III, Wilmington, NC (US); Benjamin Arcand, Minneapolis, MN (US); Robert W. Warner, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 455 days.

(21) Appl. No.: 12/489,996

(22) Filed: Jun. 23, 2009

(65) Prior Publication Data

US 2009/0324684 A1 Dec. 31, 2009

Related U.S. Application Data

(60) Provisional application No. 61/075,516, filed on Jun. 25, 2008.

(51) Int. Cl.
*A61F 2/00* (2006.01)
*A61F 13/00* (2006.01)
*A61F 2/06* (2006.01)

(52) U.S. Cl. ........ 424/426; 424/422; 623/1.38; 623/1.46
(58) Field of Classification Search .................. 424/426, 424/422; 623/1.46, 1.38
See application file for complete search history.

(56) References Cited

U.S. PATENT DOCUMENTS

| | | | |
|---|---|---|---|
| 5,468,574 A | 11/1995 | Ehrenberg et al. | |
| 5,614,549 A | 3/1997 | Greenwald et al. | |
| 5,733,925 A | 3/1998 | Kunz et al. | |
| 5,840,387 A | 11/1998 | Berlowitz-Tarrant et al. | |
| 6,156,572 A | 12/2000 | Bellamkonda et al. | |
| 6,545,097 B2 | 4/2003 | Pinchuk et al. | |
| 6,730,699 B2 | 5/2004 | Li et al. | |
| 2003/0087111 A1 | 5/2003 | Hubbell et al. | |
| 2005/0002865 A1 | 1/2005 | Klaveness et al. | |
| 2005/0187146 A1 | 8/2005 | Helmus et al. | |
| 2005/0208100 A1 | 9/2005 | Weber et al. | |
| 2005/0261756 A1* | 11/2005 | Siren | 623/1.15 |
| 2006/0052863 A1* | 3/2006 | Harder et al. | 623/1.38 |
| 2007/0129792 A1* | 6/2007 | Picart et al. | 623/1.46 |
| 2007/0154513 A1 | 7/2007 | Atanasoska et al. | |

FOREIGN PATENT DOCUMENTS

| | | | |
|---|---|---|---|
| EP | 1319416 A1 * | 6/2003 | |
| EP | 1579875 A1 | 9/2005 | |
| WO | 2004/022123 A1 | 3/2004 | |
| WO | 2005/115496 A1 | 5/2005 | |

OTHER PUBLICATIONS

K.J. McKenzie et al., "Nanoporous iron oxide membranes: layer-by-layer deposition and electrochemical characterisation of processes within nanopores", New J. Chem., 26,2002,625-629.

K.J. McKenzie et al., Journal of Electroanalytical Chemistry 579 (2005) 267-275.
K.J. McKenzie et al., "Accumulation and Reactivity of the Redox Protein Cytochrome c in Mesoporous Films of TiO2 Phytate" Langmuir 19 (2003) 4327-4331.
K.J. McKenzie et al., "TiO2 phytate films as hosts and conduits for cytochrome c electrochemistry", Bioelectrochemistry 66 (2005) 41-47.
L. Yang et al., "Assembly of electroactive layer-by-layer films of myoglobin and small-molecular phytic acid", Electrochemistry Communications 9 (2007) 1057-1061.
A.M. Shamsuddin et al., "Minireview IP6: A Novel Anti-Cancer Agent" Life Sciences, 61(4), 1997,343-354.
M. Verghese et al., "Anticarcinogenic effect of phytic acid (IP6): Apoptosis as a possible mechanism of action" LWT 39 (2006) 1093-1098.
Muraoka et al., "Inhibition of xanthine oxidase by phytic acid and its antioxidative action", Life Sciences 74 (2004) 1691-1700.
L. Jianrui et al., "Study on the corrosion resistance of phytic acid conversion coating for magnesium alloys", Surface & Coatings Technology 201 (2006) 1536-1541.
J. M. Caves et al., "The evolving impact of microfabrication and nanotechnology on stent design" J. Vasc. Surg. (2006) 44: 1363-8.
C.A. Paddon et al., "Hemoglobin adsorption into TiO2 phytate multilayer films: particle size and conductivity effects", Electrochemistry Communications 6 (2004) 1249-1253.
G. Zhao et al., "Fabrication, characterization of Fe3O4 multilayer film and its application in promoting direct electron transfer of hemoglobin", Electrochemistry Communications 8 (2006) 148-154.
V. Gauvreau et al., "Micropattern Printing of Adhesion, Spreading, and Migration Peptides on Poly(tetrafluoroethylene Films to Promote Endothelialization", Bioconjug Chem., Sep.-Oct. 16, 2005(5), 1088-97.
L. Holle et al., "In Vitro Targeted Killing of Human Endothelial Cells by Co-Incubation of Human Serum and NGR Peptide Conjugated Human Albumin Protein Bearing α (1-3) Galactose Epitopes", Oncol. Rep. Mar. 2004; 11(3):613-6.
Duncan et al., "Polymer-drug conjugates, PDEPT and PELT: basic principles for design and transfer from the laboratory to clinic", Journal of Controlled Release, 74 (2001)135-146.
Duncan, "The Dawning Era of Polymer Therapeutics", Nature Reviews/Drug Discovery, vol. 2, May 2003, 347. J. G. Qasem et al, "Kinetics of Paclitaxel 2'-N-methylpyridinium Mesylate Decomposition", AAPS PharmSciTech 2003, 4(2) Article 21.
E.W. Damen et al., "Paclitaxel Esters of Malic Acid as Prodrugs with Improved Water Solubility," Bioorg. Med. Chem., Feb. 8, 2000(2), pp. 427-32).
C. Li, "P oly(L-glutamic acid)—anticancer drug conjugates", Advanced Drug Delivery Reviews 54 (2002) 695-713.
Murali Sastry and Ashavani Kumar, Applied Physics Letters, vol. 78, No. 19, May 7, 2001, 2943.
Y. Luo et al., "A Hyaluronic Acid-Taxol Antitumor Bioconjugate Targeted to Cancer Cells" Biomacromolecules 1 (2000) 208-218.
S.C. Pillai et al., "Self-assembled arrays of ZnO nanoparticles and their application as varistor materials", J. Mater. Chem., 2004, 14, 1572-1578.

* cited by examiner

*Primary Examiner* — Abigail Fisher
(74) *Attorney, Agent, or Firm* — Mayer & Williams PC; David B. Bonham; Keum J. Park

(57) ABSTRACT

According to an aspect of the present invention, medical devices are provided which comprise a metallic region and a coating on all or part of the metallic region that comprises a multivalent acid.

27 Claims, 2 Drawing Sheets

MEDICAL DEVICES HAVING SURFACE COATINGS

RELATED APPLICATIONS

This application claims priority from U.S. provisional application 61/075,516, filed Jun. 25, 2008, which is incorporated by reference herein in its entirety.

FIELD OF THE INVENTION

The present invention relates to medical devices and more particularly to implantable or insertable medical devices having surface coatings.

BACKGROUND OF THE INVENTION

Multivalent acids have various interesting properties, including their ability to form ionic and/or covalent crosslinks as well as their ability to undergo progressive deprotonation with an increase in pH.

As a specific example, phytic acid, also known as myo-inositol hexakis(di-hydrogen phosphate), inositol hexaphosphoric acid and 1,2,3,4,5,6-cyclohexanehexolphosphoric acid, is a well-known naturally occurring acid with six phosphate functional groups attached to each carbon of a cyclohexane ring, i.e.,

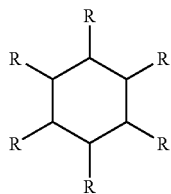

where

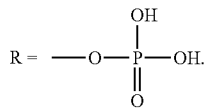

Phytic acid has twelve dissociable protons, six of which are reported to be strongly acidic with an approximate $pK_a$ value of 1.5, the following three of which are reported to be weakly acidic with $pK_a$ values between 5.7 and 7.6, and the final three of which are reported to be very weakly acidic with $pK_a$ values greater than 10. See L. Yang et al. *Electrochemistry Communications* 9 (2007) 1057-1061 and the references cited therein.

Furthermore, certain multivalent acids, including phytic acid, have been shown to have therapeutic capabilities. For example, A. M. Shamsuddin et al., *Life Sciences*, 61(4), 1997, 343-354 present a review regarding the anticancer effects of phytic acid. See also M. Verghese et al., *LWT* 39 (2006) 1093-1098. One explanation posited for the anticancer effects of phytic acid is its antioxidant properties. Muraoka et al., *Life Sciences* 74 (2004) 1691-1700.

SUMMARY OF THE INVENTION

According to an aspect of the invention, medical devices are provided which comprise a metallic region and a coating on all or part of the metallic region that comprises a multivalent acid.

Other aspects of the invention concern methods of making such devices.

The above and other aspects, as well as various embodiments and advantages of the present invention will become apparent to those of ordinary skill in the art upon review of the Detailed Description and Claims to follow.

DETAILED DESCRIPTION OF THE INVENTION

Figure 1A:
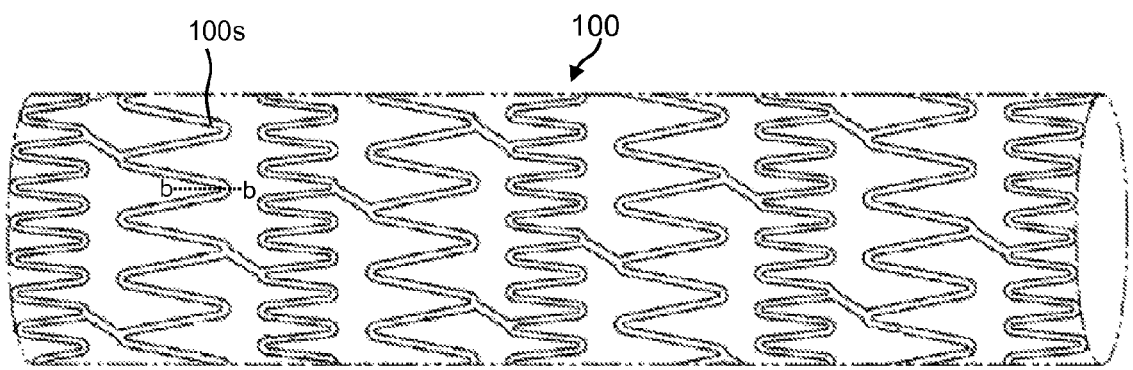
FIG. 1A is a schematic perspective view of a stent in accordance with an embodiment of the invention.

According to an aspect of the present invention, medical devices are provided which comprise a metallic region and a coating on all or part of the metallic region that comprises a multivalent acid.

According to another aspect of the invention, medical devices are provided which comprise a bioerodable metallic region and a bioerodable coating on all or part of the metallic region that provides one or more of the following functions: (a) reduces the rate of bioerosion of the metallic region, (b) delays the onset of bioerosion of the metallic region, (c) provides an anti-tumor effect, (d) provides an anti-oxidant effect, (e) provides for drug elution and (f) promotes rapid re-endothelialization.

As used herein a "metallic" region is one that contains one or more metals, typically 50 wt % or more, for example, from 50 wt % to 75 wt % to 90 wt % to 95 wt % to 97.5 wt % to 99 wt % or more.

Examples of metallic regions for use in the present invention may be selected, for example, from the following: (a) substantially pure metals, including gold, platinum, palladium, iridium, osmium, rhodium, titanium, zirconium, tantalum, tungsten, niobium, ruthenium, alkaline earth metals (e.g., magnesium), iron and zinc, and (b) metal alloys, including metal alloys comprising iron and chromium (e.g., stainless steels, including platinum-enriched radiopaque stainless steel), niobium alloys, titanium alloys, nickel alloys including alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), and alloys comprising nickel and chromium (e.g., inconel alloys), and metal alloys such as those described in Pub. No. US 2002/0004060 A1, entitled "Metallic implant which is degradable in vivo," which include metal alloys whose main constituent is selected from alkali metals, alkaline earth metals, iron, and zinc, for example, metal alloys containing magnesium, iron or zinc as a main constituent and one or more additional constituents selected from one or more of the following: alkali metals such as Li, alkaline-earth metals such as Ca and Mg, transition metals such as Mn, Co, Ni, Cr, Cu, Cd, Zr, Ag, Au, Pd, Pt, Re, Fe and Zn, Group 13 metals such as Al, and Group 14 elements such as C, Si, Sn and Pb.

Thus such metallic regions can be biostable, defined herein as maintaining 90% or more (i.e., 90% to 95% to 98% to 99% or more) of its mass in vivo over a period of 2 years or bioerodable, defined herein as losing more than 10% (i.e., 10% to 25% to 50% to 75% to 90% to 95% to 98% to 99% or more) of its mass in vivo over a period of 2 years. Other terms may be used herein other than bioerodable, including biodegradable, biocorrodable, bioresorbable, bioabsorbable, and so forth.

As used herein a "multivalent acid" is an acidic molecule that contains two or more acidic functional groups, for example, selected from carboxyl groups, phosphoric acid groups, sulfonic acid groups, and so forth.

In certain embodiments, the multivalent acid comprises an aromatic or non-aromatic multi-carbon ring and plurality of acidic functional groups substituted along the ring, in certain cases substituted on each carbon within the ring. Examples include 1,2,3,4,5,6-cyclohexanehexolphosphoric acid (phytic acid) and 1,2,3,4,5,6-cyclohexanehexacarboxylic acid, i.e.,

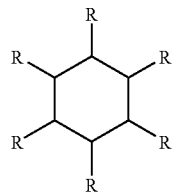

where R=—COOH, among various others.

As used herein terms such as "multivalent acid," "phytic acid" and "1,2,3,4,5,6-cyclohexanehexacarboxylic acid" embrace the acids as well as the various ionized forms thereof (e.g., salts such as sodium, potassium, etc.)

Coating thicknesses for the multivalent-acid-containing coatings of the invention may vary widely, ranging, for example, from 10 nm or less to 100 nm to 250 nm to 500 nm to 1000 nm to 2500 nm to 5000 nm to 10000 nm or more.

Examples of medical devices benefiting from the present invention vary widely and include implantable or insertable medical devices, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, catheters (e.g., urological catheters or vascular catheters such as balloon catheters and various central venous catheters), guide wires, balloons, filters (e.g., vena cava filters and mesh filters for distil protection devices), embolization devices including cerebral aneurysm filler coils (including Guglilmi detachable coils and metal coils), septal defect closure devices, myocardial plugs, patches, pacemakers, pacemaker leads, defibrillation leads, and coils, neural stimulators including neural stimulation leads, ventricular assist devices including left ventricular assist hearts and pumps, total artificial hearts, shunts, valves including heart valves and vascular valves, anastomosis clips and rings, auditory (e.g., cochlear implants), tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, orthopedic prosthesis such as bone grafts, bone plates, fins and fusion devices, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, ocular implants, or other devices that are implanted or inserted into the body.

The medical devices of the present invention thus include, for example, implantable and insertable medical devices that are used for systemic diagnosis and treatment, as well as those that are used for the localized diagnosis and treatment of any tissue or organ. As used herein, "treatment" refers to the prevention of a disease or condition, the reduction or elimination of symptoms associated with a disease or condition, or the substantial or complete elimination of a disease or condition. Subjects are vertebrate subjects, more typically mammalian subjects, and include human subjects, pets and livestock.

Coronary stents such as those commercially available from Boston Scientific Corp. (such as TAXUS EXPRESS, TAXUS LIBERTE, MAGIC WALL STENT and PROMUS ELEMENT), Johnson & Johnson (CYPHER), and others are frequently prescribed for maintaining blood vessel patency. These products are based on metallic balloon expandable and self-expandable stents with biostable polymer coatings, which release antiproliferative therapeutic agents at a controlled rate and total dose for preventing restenosis of the blood vessel.

"Therapeutic agents," "drugs," "pharmaceuticals" and other related terms may be used interchangeably herein.

Figure 1B:
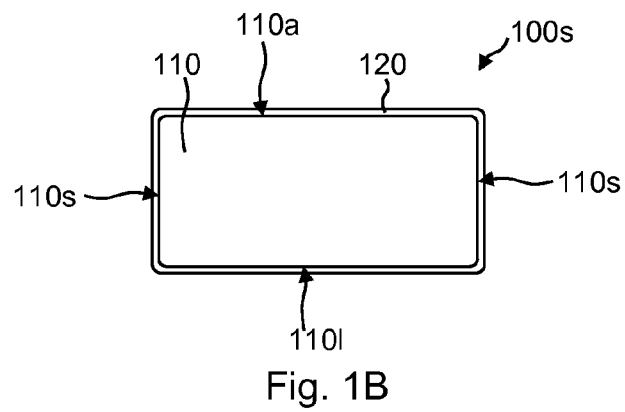
FIG. 1B is a schematic cross-sectional view of the stent FIG. 1A, taken along line b-b.

A coronary stent in accordance with an embodiment of the invention is schematically illustrated in FIGS. 1A and 1B. FIG. 1A is a schematic perspective view of a stent 100 which contains a number of interconnected struts 100s. FIG. 1B is a cross-section taken along line b-b of strut 100s of stent 100 of FIG. 1A, and shows a metallic substrate 110 (e.g., a bioerodable metallic substrate such as a magnesium substrate or a magnesium alloy substrate, among others) and a multivalent-acid-containing coating 120, which covers the entire stent strut substrate 110, including the luminal surface 110*l* (i.e., the inner, blood-contacting surface), the abluminal surface 110*a* (i.e., the outer, vessel wall-contacting surface), and side 110*s* surfaces thereof. (In other embodiments, a multivalent-acid-containing coating may cover any combination of the luminal, abluminal and side surfaces of the substrate.) Such coatings are also applicable to peripheral stents, as well numerous other devices described herein.

As a specific example, the multivalent-acid-containing coating 120 comprises phytic acid, which would slow or delay the in vivo corrosion of the stent, among other effects. Moreover, as previously indicated, phytic acid is known to have anticancer effects and therefore, when included in a stent coating, may inhibit/prevent restenosis in a manner analogous to other anticancer agents such as paclitaxel. With respect to corrosion, it has been reported that the corrosion resistance provided to magnesium alloy by a so-called "conversion coating" of phytic acid (formed by treatment in a solution containing 0.5% to 1% phytic acid at temperatures of 25 to 60° C. and at pH values in the of approx. 3 to 5 for 30 to 60 minutes) is comparable with a conventional, environmentally and biologically undesirable, hexavalent chromium conversion coating. See L. Jianrui et al., *Surface & Coatings Technology* 201 (2006) 1536-1541. The corrosion data shown in FIG. 8 of L. Jianrui et al., which were acquired in 3.5% NaCl, showed that the phytic-acid-based coating was able to provide corrosion resistance for at least one week.

In the present invention, a corrosion-resistant multivalent-acid-containing coating could be employed to slow or delay the in vivo degradation of a bioerodable metallic region (e.g., a stent substrate). For example, the above-described corrosion data suggests that a phytic acid based coating will reduce corrosion of magnesium and magnesium alloys in a 0.9% NaCl physiological environment (which is more dilute than the 3.5% test environment) for at least one week. For a vascular implant such as a stent, this would give endothelial cells the opportunity to coat/encapsulate the device. The formation of a functional endothelial cell layer is known to be effective for purposes of reducing or eliminating inflammation and thrombosis, which can occur in conjunction with the implantation of a foreign body in the vasculature. See, e.g., J. M. Caves et al., *J. Vasc. Surg.* (2006) 44: 1363-8. Other examples of bioerodable metallic materials for treatment with phytic acid (besides magnesium and magnesium alloys) include iron and iron alloys, zinc and zinc alloys and calcium and calcium alloys, among others.

In other embodiments, materials other than multivalent acids are provided in the coatings of the invention. Examples of such additional materials include ceramic particles, charged particles of various composition, charged polymers (including synthetic polyelectrolytes and various natural charged polymers such as DNA, proteins, peptides, etc.), and a variety of charged and uncharged therapeutic agents.

One way to incorporate additional materials into the coatings of the invention is via a multi-layer assembly process. By way of background, multilayer coatings can be formed on substrates by exposure to solutions or dispersions of a variety of materials, based on various bonding mechanisms, for example, covalent bonding as well as non-covalent bonding mechanisms such as hydrophobic interactions and/or electrostatic interactions, for instance, charge-charge interactions, charge-dipole interactions, and dipole-dipole interactions (including hydrogen bonding), among other mechanisms.

Solutions/dispersions may be applied to a metallic region by a variety of techniques. These techniques include, for example, full immersion techniques such as dipping techniques, spraying techniques, transfer techniques such as stamping and roll and brush coating techniques, techniques involving coating via mechanical suspension such as air suspension, ink jet techniques, spin coating techniques, web coating techniques and combinations of these processes, among others. The choice of the technique will depend on the requirements at hand. For example, deposition or full immersion techniques may be employed where it is desired to apply the species to an entire substrate, including surfaces that are hidden from view (e.g., surfaces which cannot be reached by line-of-sight techniques, such as spray techniques). On the other hand, spraying and direct transfer techniques such as stamping, roll and brush coating and ink jet printing may be employed, for instance, where it is desired to apply the species to only certain portions of the substrate (e.g., on one side of a substrate, in the form of a pattern on a substrate, etc.). For instance, such techniques may be used to selectively apply solutions/dispersions to the luminal surface of a stent, the abluminal surface and/or to the side surfaces (e.g., the ends).

In some embodiments, multivalent acid layers may be alternated with ceramic particle layers in order to build multilayer structures. Examples of ceramic particles for the practice of the present invention may be selected from particles of metal and semi-metal oxides, oxonitrides and oxocarbides, including oxides oxonitrides and oxocarbides of Periodic Table Group 14 semi-metals (e.g., Si, Ge), and oxides oxonitrides and oxocarbides of transition and non-transition metals such as Group 2 metals (e.g., Mg, Ca), Group 3 metals (e.g., Sc, Y), Group 4 metals (e.g., Ti, Zr, Hf), Group 5 metals (e.g., V, Nb, Ta), Group 6 metals (e.g., Cr, Mo, W), Group 7 metals (e.g., Mn, Tc, Re), Group 8 metals (e.g., Fe, Ru, Os), Group 9 metals (e.g., Co, Rh, Ir), Group 10 metals (e.g., Ni, Pd, Pt), Group 11 metals (e.g., Cu, Ag, Au), Group 12 metals (e.g., Zn, Cd, Hg), Group 13 metals (e.g., Al, Ga, In, Tl), Group 14 metals (e.g., Sn, Pb), Group 15 metals (e.g., Bi). In certain embodiments, ceramic particles are formed from bioactive ceramic materials (defined herein as material that promotes good adhesion with adjacent tissue, for example, bone tissue or soft tissue, with minimal adverse biological effects, for instance, the formation of connective tissue such as fibrous connective tissue), sometimes referred to as "bioceramics," including calcium phosphate ceramics (e.g., hydroxyapatite), calcium-phosphate glasses (sometimes referred to as glass ceramics, e.g., bioglass), and various metal oxide ceramics such as titanium oxide, iridium oxide, zirconium oxide, tantalum oxide and niobium oxide, among other materials. Phosphate ions such as those found in phytic acids are known to bind strongly to metal oxide surfaces. See K. J. McKenzie et al., *New J. Chem.*, 26, 2002, 625-629.

The ceramic particles for use in the present invention can vary widely in size, but commonly are nanoparticles that have at least one major dimension (e.g., the thickness for a nanoplates, the diameter for a nanospheres, nanocylinders and nanotubes, etc.) that is 100 nm or less, for example, ranging from 100 nm to 50 nm to 25 nm to 10 nm to 5 nm to 2 nm to 1 nm or less.

Multilayer coatings formed from multivalent acids and ceramic particles may be porous. Consequently, the coatings may be loaded, if desired, with charged or uncharged therapeutic agents, for example, by contacting the coating with a solution or dispersion that contains one or more therapeutic agents.

As used herein, a "porous coating" is one that comprises pores. Pore sizes may range, for example, from nanopores (i.e., pores having widths of 50 nm or less), including micropores (i.e., pores having widths smaller than 2 nm) and mesopores (i.e., pores having a widths ranging from 2 to 50 nm), to macropores (i.e., pores having widths that are larger than 50 nm). As used herein, a nanoporous surface is one that comprises nanopores, a microporous surface is one that comprises micropores, a mesoporous surface is one that comprises mesopores, and a macroporous surface is one that comprises macropores.

Details regarding the formation of multilayer coatings from multivalent acids and ceramic oxide particles may be found, for example, in McKenzie et al., *Journal of Electroanalytical Chemistry* 579 (2005) 267-275, who report layer by layer deposition of mesoporous coatings on indium tin oxide by alternating exposure to (a) $TiO_2$ (anatase sol, 30-35% in aqueous $HNO_3$, pH 1-2 diluted 1:10 with water, pH 1.5) and (b) either phytic acid (40 mM, acidified to pH 3) or cyclohexanehexacarboxylic acid (40 mM in water) as a "molecular binder", followed by calcination at 500° C. in air. With the phytic acid structures, film thickness increased on the order of 20-30 nm per $TiO_2$-phytate bilayer. The presence of phosphate from the phytic acid was found to markedly influence the surface charge of the resulting coating, with the positively charged surface said to adsorb positively charged cations such as $Ru(NH_3)_6^{3+}$, cytochrome c, tetrakis[1-octylpyridinium]-porphyrin and dopamine. For further information on cytochrome c adsorption see K. J. McKenzie et al., *Langmuir* 19 (2003) 4327-4331 and K. J. McKenzie et al., *Bioelectrochemistry* 66 (2005) 41-47 in which cytochrome c is adsorbed onto mesoporous $TiO_2$-phytate coatings. The latter reference also reports that $TiO_2$-phytate films are electron-conducting when immersed in an aqueous buffer solution (0.1 M phosphate buffer solution at pH 7). Others report the layer-by-layer assembly of phytic acid and of $TiO_2$ nanoparticles without calcination. For example, C. A. Paddon et al., *Electrochemistry Communications* 6 (2004) 1249-1253 describe layer by layer deposition on indium tin oxide of $TiO_2$ nanoparticles (ca. 6-10 nm diameter in the form of an anatase sol) and phytic acid. Hemoglobin was adsorbed to the surface. Films of 40 bilayers were reported to be approx. 800 nm in thickness. Still others have reported the use of nanoparticles other than $TiO_2$ nanoparticles. See, e.g., K. J. McKenzie et al., *New J. Chem.*, 26, 2002, 625-629 which report layer by layer deposition on indium tin oxide of a nanoporous layer coating formed from 4-5 nm $Fe_2O_3$ particles (from colloidal $Fe_2O_3$ solution) and phytic acid, followed by calcination of the resulting structure at 500° C. in air to form a nanoporous membrane. In G. Zhao, *Electrochemistry Communications* 8 (2006) 148-154, $Fe_3O_4$ (magnetite), in the form of alternating layers of chitosan-stabilized $Fe_3O_4$ nanoparticles and phytic acid were deposited on glassy carbon, indium tin oxide glass, and aluminum foil in alternating layers. Phytic acid was the outer layer. Hemoglobin (3 mg/ml) was adsorbed at the surface. For the first layer, electrodeposition was employed, followed by alternating phytic acid and chitosan-stabilized $Fe_3O_4$ nanoparticles. In addition to electrostatic effects, iron-oxide phosphate interactions were believed to be significant.

In some embodiments, multiple layers of charged chemical species may be deposited, for example, selected from multivalent acids, proteins and other charged polymers such as synthetic polyelectrolytes, charged therapeutic agents, and charged particles. In certain of these embodiments, where layers of the charged chemical species are alternated with phytic acid, due to the negatively charged nature of multivalent acids, the charged chemical species are positively charged or have domains in which there is a net positive charge. With respect to the latter, L. Yang et al., *Electrochemistry Communications* 9 (2007) 1057-1061 describe layer by layer assembly on pyrolytic graphite of phytic acid (20 mg/mL, pH 5) and myoglobin (1 mg/mL, pH 5). Not only negatively charged myoglobin at pH 5.0 was deposited, but also the positively charged myoglobin at pH 9.0 was deposited. The authors suggest that layer-by-layer assembly was possible in the latter case due to the non-uniform charge distribution on the myoglobin surface, with some of the positively charged surface groups electrostatically interacting with the negatively charged phytic acid.

By way of background, it is known that multilayer coatings can be formed on substrates based on electrostatic self-assembly of charged materials. For example, a first layer having a first surface charge is typically deposited on an underlying substrate (in the present invention, a metallic region of a medical device or portion thereof), followed by a second layer having a second surface charge that is opposite in sign to the surface charge of the first layer, and so forth. The charge on the outer layer is reversed upon deposition of each sequential layer. Commonly, 5 to 10 to 25 to 50 to 100 to 200 or more layers are applied in this technique, depending on the desired thickness of the multilayer structure. For further information concerning layer-by-layer electrostatic self-assembly methods, see, e.g., US 2005/0208100 to Weber et al., and WO/2005/115496 to Chen et al.

Certain substrates are inherently charged and thus readily lend themselves to electrostatic layer-by-layer assembly techniques. To the extent that the substrate does not have an inherent net surface charge, a surface charge may nonetheless be provided. For example, where the substrate to be coated is conductive (e.g., a metallic region in the devices of the present invention), a surface charge may be provided by applying an electrical potential to the same. As another example, a substrate can be provided with a charge by covalently coupling to species having functional groups with a positive charge (e.g., amine, imine or other basic groups) or a negative charge (e.g., carboxylic, phosphonic, phosphoric, sulfuric, sulfonic, or other acid groups). Further information on covalent coupling may be found, for example, in U.S. Pub. No. 2005/0002865. In many embodiments, a surface charge is provided on a substrate simply by adsorbing cationic or anionic species to the surface of the substrate as a first charged layer. Polyethyleneimine (PEI) is commonly used for this purpose, as it strongly promotes adhesion to a variety of substrates. Further information can be found in U.S. Pub. No. 2007/0154513 to Atanasoska et al. Moreover, as indicated above, multivalent acids such as phytic acid, which are negatively charged, readily interact with metallic surfaces to form surface coatings.

Regardless of the method by which a given substrate is provided with a surface charge, once a sufficient surface charge is provided (e.g., via application of an electrical potential, chemical conversion of the surface, adsorption/binding of charged species onto the surface, etc.), the substrate can be readily coated with alternating layers of charged materials. Examples of such layers include layers that contain (a) multivalent acids, (b) charged polymers, (c) charged therapeutic agents, and (d) charged particles. Multilayer regions are formed by alternating exposure to solutions/dispersions containing the charged materials, which are commonly (but not necessarily—see L. Yang et al. supra) of opposite net charge. The layers self-assemble, thus forming a multilayered region over the substrate.

"Charged polymers" are polymers having multiple charged groups. Such polymers may also be referred to herein as "polyelectrolytes". Charged polymers thus include a wide range of species, including polycations and their precursors (e.g., polybases, polysalts, etc.), polyanions and their precursors (e.g., polyacids, polysalts, etc.), polymers having multiple anionic and cationic groups (e.g., polymers having multiple acidic and basic groups such as are found in various proteins), ionomers (charged polymers in which a small but significant proportion of the constitutional units carry charges), and so forth. Typically, the number of charged groups is so large that the polymers are soluble in polar solvents (particularly water) when in ionically dissociated form (also called polyions). Some charged polymers have both anionic and cationic groups (e.g., proteins) and may have a net negative charge (e.g., because the anionic groups contribute more charge than the cationic groups—referred to herein as polyanions), a net positive charge (e.g., because the cationic groups contribute more charge than the anionic groups—referred to herein as polycations), or may have a neutral net charge (e.g., because the cationic groups and anionic groups contribute equal charge). In this regard, the net charge of a particular charged polymer may change with the pH of its surrounding environment. Charged polymers containing both cationic and anionic groups may be categorized herein as either polycations or polyanions, depending on which groups predominate.

Specific examples of suitable polycations may be selected, for instance, from the following: polyamines, including polyamidoamines, poly(amino methacrylates) including poly(dialkylaminoalkyl methacrylates) such as poly(dimethylaminoethyl methacrylate) and poly(diethylaminoethyl methacrylate), polyvinylamines, polyvinylpyridines including quaternary polyvinylpyridines such as poly(N-ethyl-4-vinylpyridine), poly(vinylbenzyltrimethylamines), polyallylamines such as poly(allylamine hydrochloride) (PAH) and poly(diallyidialklylamines) such as poly(diallyidimethylammonium chloride), spermine, spermidine, hexadimethrene bromide(polybrene), polyimines including polyalkyleneimines such as polyethyleneimines, polypropyleneimines and ethoxylated polyethyleneimines, basic peptides and proteins, including histone polypeptides and homopolymer and copolymers containing lysine, arginine, ornithine and combinations thereof including poly-L-lysine, poly-D-lysine, poly-L,D-lysine, poly-L-arginine, poly-D-arginine, poly-D, L-arginine, poly-L-ornithine, poly-D-ornithine, and poly-L, D-ornithine, gelatin, albumin, protamine and protamine sulfate, and polycationic polysaccharides such as cationic starch and chitosan, as well as copolymers, derivatives and combinations of the preceding, among various others.

Specific examples of suitable polyanions may be selected, for instance, from the following: polysulfonates such as polyvinylsulfonates, poly(styrenesulfonates) such as poly(sodium styrenesulfonate) (PSS), sulfonated poly(tetrafluoroethylene), sulfonated polymers such as those described in U.S. Pat. No. 5,840,387, including sulfonated styrene-ethylene/butylene-styrene triblock copolymers, sulfonated styrenic homopolymers and copolymers such as a sulfonated versions of the polystyrene-polyolefin copolymers described in U.S. Pat. No. 6,545,097 to Pinchuk et al., which polymers may be sulfonated, for example, using the processes described in U.S. Pat. No. 5,840,387 and U.S. Pat. No. 5,468,574, as well as sulfonated versions of various other homopolymers and copolymers, polysulfates such as polyvinylsulfates, sulfated and non-sulfated glycosaminoglycans as well as certain proteoglycans, for example, heparin, heparin sulfate, chondroitin sulfate, keratan sulfate, dermatan sulfate, polycarboxylates such as acrylic acid polymers and salts thereof (e.g., ammonium, potassium, sodium, etc.), for instance, those available from Atofina and Polysciences Inc., methacrylic acid polymers and salts thereof (e.g., EUDRAGIT, a methacrylic acid and ethyl acrylate copolymer), carboxymethylcellulose, carboxymethylamylose and carboxylic acid derivatives of various other polymers, polyanionic peptides and proteins such as glutamic acid polymers and copolymers, aspartic acid polymers and copolymers, polymers and copolymers of uronic acids such as mannuronic acid, galatcuronic acid and guluronic acid, and their salts, alginic acid and sodium alginate, hyaluronic acid, gelatin, and carrageenan, polyphosphates such as phosphoric acid derivatives of various polymers, polyphosphonates such as polyvinylphosphonates, polysulfates such as polyvinylsulfates, as well as copolymers, derivatives and combinations of the preceding, among various others.

As seen from the above, charged polymers include those comprising poly(amino acid) sequences (e.g., peptides, proteins, etc.), which can have a cationic, anionic or neutral net charge, depending on the pH. Further examples of charged polymers include those containing poly(amino acid) sequences that promote cell adhesion and/or cell growth, among other effects. For example, polypeptides containing RGD sequences (e.g., GRGDS) and WQPPRARI sequences are known to direct spreading and migrational properties of endothelial cells. See V. Gauvreau et al., Bioconjug Chem., September-October 2005, 16(5), 1088-97. REDV tetrapeptide has been shown to support endothelial cell adhesion but not that of smooth muscle cells, fibroblasts, or platelets, and YIGSR pentapeptide has been shown to promote epithelial cell attachment, but not platelet adhesion. More information on REDV and YIGSR peptides can be found in U.S. Pat. No. 6,156,572 and Pub. No. US 2003/0087111. A further example of a cell-adhesive sequence is NGR tripeptide, which binds to CD13 of endothelial cells. See, e.g., L. Holle et al., "In vitro targeted killing of human endothelial cells by co-incubation of human serum and NGR peptide conjugated human albumin protein bearing alpha (1-3) galactose epitopes," Oncol. Rep. March 2004; 11 (3):613-6. Other charged polymers useful for cell adhesion may be selected from suitable proteins, glycoproteins, polysaccharides, proteoglycans, glycosaminoglycans and subunits and fragments of the same, for example, those set forth in Pub. No. US 2005/0187146 to Helmus et al. Specific examples of proteins include collagen (e.g., type II, etc.), fibronectin, fibrinogen and laminin, among others.

By "charged therapeutic agent" is meant a therapeutic agent that has an associated charge. For example, a therapeutic agent may have an associated charge because it is inherently charged (e.g., because it has one or more acidic and/or or basic groups, which may be in salt form). A few examples of inherently charged cationic therapeutic agents include amiloride, digoxin, morphine, procainamide, and quinine, among many others. Examples of anionic therapeutic agents include heparin and DNA, among many others. A therapeutic agent may also have an associated charge because it has been chemically modified to provide it with one or more charged functional groups. For instance, conjugation of water insoluble or poorly soluble drugs, including anti-tumor agents such as paclitaxel, to hydrophilic polymers has recently been carried out in order to solubilize the drugs (and in some cases to improve tumor targeting and reduce drug toxicity). Similarly, cationic or anionic versions of water insoluble or poorly soluble drugs have also been developed. Taking paclitaxel as a specific example, various cationic forms of this drug are known, including paclitaxel N-methyl pyridinium mesylate and paclitaxel conjugated with N-2-hydroxypropyl methyl amide, as are various anionic forms of paclitaxel, including paclitaxel-poly(l-glutamic acid), paclitaxel-poly(l-glutamic acid)-PEO. See, e.g., U.S. Pat. No. 6,730,699; Duncan et al., Journal of Controlled Release, 74 (2001)135; Duncan, Nature Reviews/Drug Discovery, Vol. 2, May 2003, 347; J. G. Qasem et al, AAPS Pharm Sci Tech 2003, 4(2) Article 21. In addition to these, U.S. Pat. No. 6,730,699, also describes paclitaxel conjugated to various other charged polymers including poly(d-glutamic acid), poly(dl-glutamic acid), poly(l-aspartic acid), poly(d-aspartic acid), poly(dl-aspartic acid), poly(l-lysine), poly(d-lysine), poly(dl-lysine), copolymers of the above listed polyamino acids with polyethylene glycol (e.g., paclitaxel-poly(l-glutamic acid)-PEO), as well as poly(2-hydroxyethyl 1-glutamine), chitosan, carboxymethyl dextran, hyaluronic acid, human serum albumin and alginic acid. Still other forms of paclitaxel include carboxylated forms such as 1'-malyl paclitaxel sodium salt (see, e.g. E. W. DAmen et al., "Paclitaxel esters of malic acid as prodrugs with improved water solubility," Bioorg. Med. Chem., February 2000, 8(2), pp. 427-32). Polyglutamate paclitaxel, in which paclitaxel is linked through the hydroxyl at the 2' position to the Δ carboxylic acid of the poly-L-glutamic acid (PGA), is produced by Cell Therapeutics, Inc., Seattle, Wash., USA. (The 7 position hydroxyl is also available for esterification.) This molecule is said to be cleaved in vivo by cathepsin B to liberate diglutamyl paclitaxel. In this molecule, the paclitaxel is bound to some of the carboxyl groups along the backbone of the polymer, leading to multiple paclitaxel units per molecule. For further information, see, e.g., R. Duncan et al., "Polymer-drug conjugates, PDEPT and PELT: basic principles for design and transfer from the laboratory to clinic," Journal of Controlled Release 74 (2001) 135-146, C. Li, "Poly(L-glutamic acid)—anticancer drug conjugates," Advanced Drug Delivery Reviews 54 (2002) 695-713; Duncan, Nature Reviews/Drug Discovery, Vol. 2, May 2003, 347; Qasem et al, AAPS Pharm Sci Tech 2003, 4(2) Article 21; and U.S. Pat. No. 5,614,549. A therapeutic agent may also have an associated charge because it is attached to a charged particle, for example, attached to a charged nanoparticle (e.g., a charged particle having a cross-sectional dimension of 100 nm or less, for example, a spherical particle or a rod-shaped particle having a diameter of 100 nm or less) or because it is encapsulated within a charged particle, for example, encapsulated within a charged nanocapsule or within a charged micelle, among others. Using the above and other strategies, paclitaxel and innumerable other therapeutic agents may be covalently linked or otherwise associated with a variety of charged species, including charged polymer molecules and charged particles, thereby forming charged drugs and pro-drugs which can be assembled in a layer-by-layer process. Such charged species may be adapted for cleavage from the drug/prodrug prior to administration or upon administration (e.g., due to enzymatic cleavage, etc.).

Examples of charged particles include those that are inherently charged or those that are charged, for example, using one of the suitable techniques described above for use in providing charged substrates. For example, particles may be exposed to a solution of PEI to create negatively charged particles. If desired, the charge on a particle can be reversed by exposing it to a solution containing a polyelectrolyte of opposite charge.

The charged particles for use in the coatings of present invention can vary widely in size, but typically are nanoparticles that have at least one major dimension (e.g., the thickness for a nanoplates, the diameter for a nanospheres, nano-cylinders and nanotubes, etc.) that is less than 1000 nm, more typically less than 100 nm. Hence, for example, nanoplates typically have at least one dimension (e.g., thickness) that is less than 1000 nm, other nanoparticles typically have at least two orthogonal dimensions (e.g., thickness and width for nano-ribbons, diameter for cylindrical and tubular nanoparticles, etc.) that are less than 1000 nm, while still other nanoparticles typically have three orthogonal dimensions that are less than 1000 nm (e.g., the diameter for nanospheres).

A variety of charged particles may be used in the coatings of the present invention including, for example, carbon, ceramic and metallic nanoparticles including nanoplates, nano-ribbons, nanotubes, and nanospheres, and other nanoparticles. Specific examples of nanoplates include synthetic or natural phyllosilicates including clays and micas (which may optionally be intercalated and/or exfoliated) such as montmorillonite, hectorite, hydrotalcite, vermiculite and laponite. Specific examples of nanotubes and nanofibers include single-wall, so-called "few-wall," and multi-wall carbon nanotubes, vapor grown carbon fibers, alumina nanofibers, titanium oxide nanofibers, tungsten oxide nanofibers, tantalum oxide nanofibers, zirconium oxide nanofibers, and silicate nanofibers such as aluminum silicate nanofibers. Specific examples of further nanoparticles (e.g., nanoparticles having three orthogonal dimensions that are less than 1000 nm) include fullerenes (e.g., "Buckey balls"), silica nanoparticles, gold nanoparticles, aluminum oxide nanoparticles, titanium oxide nanoparticles, tungsten oxide nanoparticles, tantalum oxide nanoparticles, zirconium oxide nanoparticles, dendrimers, and monomeric silicates such as polyhedral oligomeric silsequioxanes (POSS), including various functionalized POSS and polymerized POSS. With respect to functionalized gold nanoparticles, it is noted that these particles may help to create a radio-opaque layer. Gold nanoparticles may be made positively charged by applying an outer layer of lysine to the same. See, for example, "DNA-mediated electrostatic assembly of gold nanoparticles into linear arrays by a simple drop-coating procedure," Murali Sastrya and Ashavani Kumar, *Applied Physics Letters*, Vol. 78, No. 19, 7 May 2001, 2943.

Figure 2A:
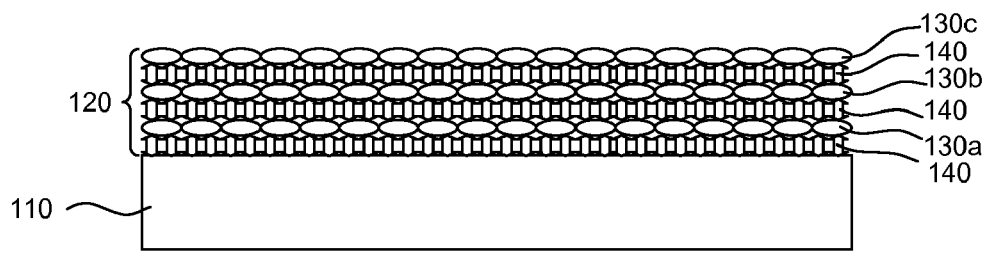
FIGS. 2A-2C are schematic illustrations of three coating schemes for medical device substrates, in accordance with various embodiments of the invention.
Figure 2B:
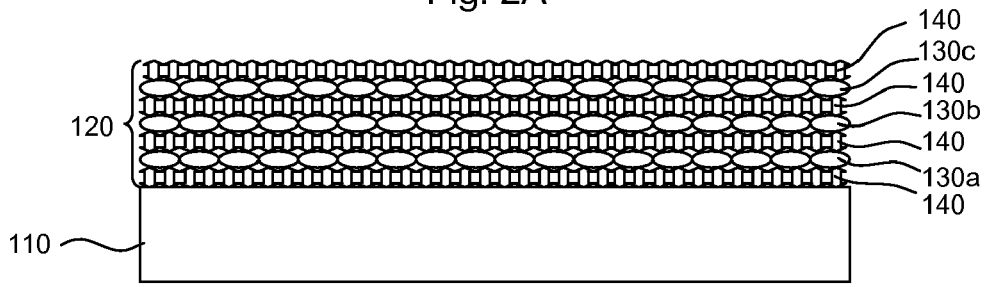
Figure 2C:
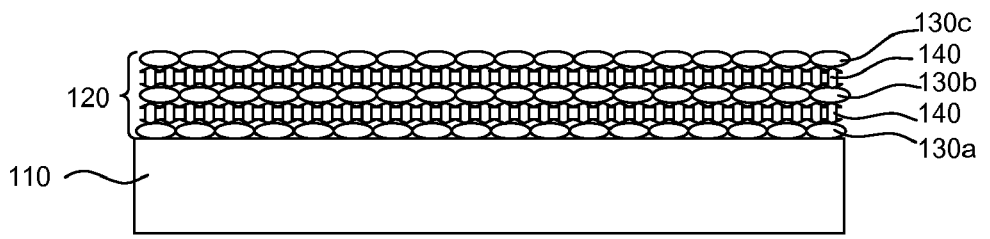

FIG. 2A-2C are schematic illustrations of three medical device coatings in accordance with the present invention. Each of these figures comprises a substrate 110 and a multivalent-acid-containing coating 120. The multivalent-acid-containing coating 120 in each of these figures comprises multiple polyvalent acid layers 140 (e.g. phytic acid, which as noted above has various interesting properties including the fact that they are negatively charged, can bind to metals and metal oxides, and have antioxidant properties, among others). 2-4 polyvalent acid layers are shown in these figures, but 1 layer or 5 or more layers, e.g., 5 to 10 to 20 to 50 to 100 or more layers, are possible. The multivalent-acid-containing coating 120 in each of these figures also comprises multiple additional layers 130a, 130b, 130c, which may be independently selected, for example, from ceramic particles, metallic particles, charged polymers, charged therapeutic agents, and charged particles as described above, among other possibilities. 3 polyvalent acid layers are shown in the figures, but 1, 2, 4 or more layers, e.g., 5 to 10 to 20 to 50 to 100 or more layers, are possible. In some embodiments, a polyvalent acid layer 140 is employed as the innermost layer (e.g., for purposes of providing an anti-corrosive layer). See, e.g., FIGS. 2A and 2B. In some embodiments, a polyvalent acid layer 140 is used as the outermost layer (e.g., for purposes of attracting ionic species, including proteins, in vivo). See, e.g., FIG. 2B. In some embodiments, layer 130a is the innermost layer (e.g., for purposes of promoting adhesion to the substrate). See, e.g., FIG. 2C. In some embodiments, layer 130c is the outermost layer (e.g., for purposes of promoting endothelial growth, in vivo). See, e.g., FIGS. 2A and 2C. The layers 130a, 130b, 130c may be the same or different (e.g., independently selected from ceramic particles, metallic particles, charged polymers, charged therapeutic agents, charged particles, etc.). For example, layers 130a, 130b may be particles of metal or semi-metal oxygen compounds (e.g., oxides, oxycarbides, oxynitrides, etc.) and layer 130c may be an endothelialization-promoting protein or peptide, or it may be formed from bioactive ceramic particles. (Although not illustrated, layers 140 may also be the same or different, for example, formed from phytic acid, 1,2,3,4,5,6-cyclohexanehexacarboxylic acid and/or other multivalent acids.) Although not illustrated, coatings like those shown in FIGS. 2A-2C may be imbibed with a charged or uncharged therapeutic agent after the coating is formed for purposes of drug elution in vivo.

Another embodiment of the invention is illustrated in FIG. 3. FIG. 3 is like FIG. 2A except that the substrate 110 (e.g., a biostable or bioerodable substrate) provided further comprises depressions (e.g., channels, blind holes, etc.) that contain a therapeutic-agent-containing region 150 (which may contain another material such as one or more pharmaceutically acceptable excipients) and a bioerodable metallic layer 160 disposed over the therapeutic-agent-containing region 150. The bioerodable metallic layer 160 may be provided over the therapeutic-agent-containing region 150 using a suitable technique, such as PVD, which does not substantially inactivate or destroy the therapeutic agent upon application. In the device of FIG. 3, the therapeutic agent is released in vivo after the bioerosion of the metallic layer 160.

Figure 3A:
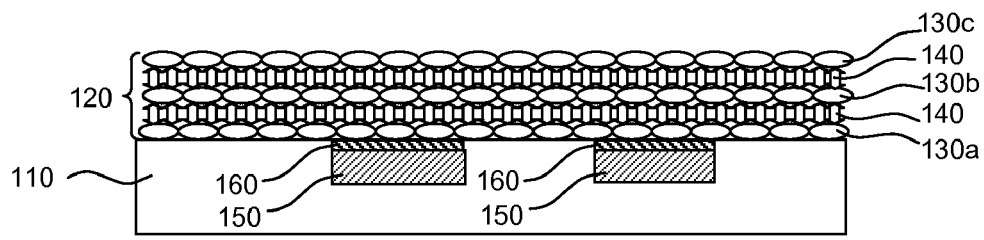
FIGS. 3A and 3B are schematic illustrations of a medical device substrates with coatings in accordance other embodiments of the invention.
Figure 3B:
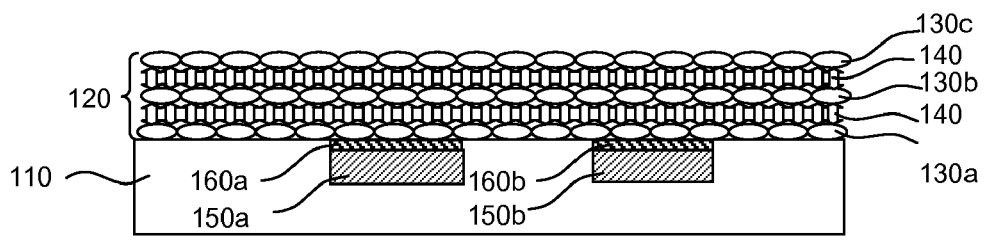

FIG. 3B is similar to FIG. 3A, except that the device comprises a first therapeutic-agent-containing region 150a comprising a first therapeutic agent and a second therapeutic-agent-containing region 150b comprising a second therapeutic agent. The first therapeutic agent may be the same or different than the second therapeutic agent. A first bioerodable metallic layer 160a is provided over the first therapeutic-agent-containing region 150a and a second bioerodable metallic layer 160b is disposed over the second therapeutic-agent-containing region 150b. The first bioerodable metallic layer 160a may have a thickness and/or composition that is different than that of the second bioerodable metallic layer 160b, allowing for enhanced control over the release characteristics of one or more therapeutic agents.

Where a therapeutic agent is included in the coatings of the invention (e.g., imbibed, electrostatically incorporated as a charged layer, etc.), the therapeutic agent content may vary widely, ranging, for example, from 1 wt % or less to 2 wt % to 5 wt % to 10 wt % to 25% of the coating or more. Where a therapeutic agent is included in one or more depressions in a substrate (e.g., by deposition, etc.), the therapeutic agent content may also vary widely, ranging, for example, from 1 wt % or less to 10 wt % to 25 wt % to 50 wt % to 75 wt % to 90 wt % to 95 wt % or more.

A wide variety of therapeutic agents may be employed in conjunction with the present invention, including genetic therapeutic agents, non-genetic therapeutic agents and cells, which may be used for the treatment of a wide variety of diseases and conditions. Numerous therapeutic agents are described here.

Suitable therapeutic agents for use in connection with the present invention may be selected, for example, from one or more of the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, antimicrobial peptides such as magainins, aminoglycosides and nitrofurantoin; (m) cytotoxic agents, cytostatic agents and cell proliferation affectors; (n) vasodilating agents; (o) agents that interfere with endogenous vasoactive mechanisms, (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta-blockers, (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists such as rosiglitazone, pioglitazone, netoglitazone, fenofibrate, bexaotene, metaglidasen, rivoglitazone and tesaglitazar, (bb) prostaglandin E agonists such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, (ff) phospholipids including phosphorylcholine, phosphatidylinositol and phosphatidylcholine, and (gg) VLA-4 antagonists and VCAM-1 antagonists.

Preferred therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well a derivatives of the forgoing, among others.

Numerous therapeutic agents, not necessarily exclusive of those listed above, have been identified as candidates for vascular and other treatment regimens, for example, as agents targeting restenosis (antirestenotics). Such agents are useful for the practice of the present invention and suitable examples may be selected from one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid, SOD (orgotein) and SOD mimics, verteporfin, rostaporfin, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline, and (dd) glucose cross-link breakers such as alagebrium chloride (ALT-711).

Numerous additional therapeutic agents useful for the practice of the present invention are also disclosed in U.S. Pat. No. 5,733,925 to Kunz et al.

Various specific examples of the invention follow. In the examples, stents are completely coated with the various phytate-containing coatings. In other embodiments, the coatings may be applied to only the abluminal stent surface of the stent, only the luminal surface, and so forth. In other embodiments, devices other than stents may be used as substrates.

EXAMPLE 1

Vascular stents made of magnesium metal are electropolished using an applied potential of 3V for 10-20 seconds in a solution of 3 parts of phosphoric acid and 5 parts of 95% ethanol, followed by drying in hot air. A so-called "conversion layer" is then formed on the stents by immersing the stents in various solutions containing a range of phytic acid concentrations (0.1-3 wt %) under different pH values (1-9) and different temperatures (25-80° C.) for different times (10-240 minutes). The stents with the thus-formed conversion layers are then taken out of the treatment solution, rinsed with distilled water and dried at room temperature.

Stents prepared with the phytate conversion coating are further coated with a $TiO_2$ nanoparticle-phytate coating using a layer-by-layer process along the lines described in K. J. McKenzie et al., *Bioelectrochemistry* 66 (2005) 41-47. Solution A consists of $TiO_2$ sol (anatase sol, TKS-202, typically 6 nm diameter, 30-37% acidified with nitric acid, Tayca Corp, Osaka, Japan) which is diluted 100-fold with distilled water. Solution B is prepared by dissolving sodium phytate (Aldrich) to give a 40 mM solution in water, followed by acidification with perchloric acid to pH 3. The stents are immersed in each solution for 30-60 sec with intermediate rinsing steps in distilled water (alternating Solution A and Solution B, beginning with Solution A and ending in Solution B). The stents are immersed in each solution up to 50 times. The stents thus coated with this repeating bi-layer phytate-based coating are then immersed in an aqueous 0.1 M phosphate buffered (pH 7) solution containing 0.05 mM collagen (or fibronectin) for 10-30 seconds and dried.

EXAMPLE 2

Example 1 is repeated, except that a $Fe_2O_3$, sol is used in place of the $TiO_2$ sol in the nanoparticles deposition steps. Colloidal iron oxide may be prepared as described in K. J. McKenzie et al., *New J. Chem.,* 26 (2002) 625-629. Specifically, aqueous 20 mM $FeCl_3$ ($FeC;_3.6H_2O$, Fischer) is added dropwise into boiling water. The resulting nanoparticles are 4-5 nm diameter in size and form a stable sol with ca. 2 mM content of Fe.

EXAMPLE 3

Example 1 is repeated, except that a ZnO sol is used in place of the $TiO_2$ sol in the nanoparticles deposition steps.

EXAMPLE 4

Example 1 is repeated, except that a MgO sol is used in place of the $TiO_2$ sol in the nanoparticles deposition steps.

EXAMPLE 5

Example 1 is repeated, except that a CaO sol is used in place of the $TiO_2$ sol in the nanoparticles deposition steps.

EXAMPLE 6

Example 1 is repeated, except that hemoglobin is applied as a final layer by equilibrating the $TiO_2$ phytate modified stents in a solution of hemoglobin (1 mg/mL) prepared in 0.1M phosphate buffer at pH 5.5 followed by rinsing with distilled water.

EXAMPLE 7

Stents are first provided with a phytate conversion layer as in Example 1. These stents are then treated in an alternating fashion according to the following two processes: (a) immersion a colloidal $Fe_2O_3$ solution for 1 min, followed by rinsing with distilled water, (b) immersion into aqueous 40 mM phytic acid for 1 min, followed by rinsing with distilled water. Suitable solutions are described in K. J. McKenzie et al., *New J. Chem.*, 26, 2002, 625-629. The foregoing steps are repeated up to 50 times. The as-deposited phytic-acid-containing coating is then treated for 60 min at 500° C. in air in a tube furnace, resulting in calcination and formation of a nanoporous film.

EXAMPLE 8

Stents are first provided with a phytate conversion layer as in Example 1. Then the stents are coated in a layer-by-layer process. First, the stents are dipped in an $Fe_3O_4$/chitosan dispersion (1.5 mg/ml), which may be prepared as described in G. Zhao et al., *Electrochemistry Communications* 8 (2006) 148-154. Then, the stents are dipped into phytic acid solution (40 mmol/l, pH 5.0) for about 20 min, washed with water and dried. After that, the stents are dipped into the $Fe_3O_4$/chitosan dispersions for about 20 min, washed with water and dried. By repeating the dipping procedures in the two different solutions, the multilayer films of ($Fe_3O_4$/chitosan-phytic acid) are obtained.

EXAMPLE 9

The procedure of Example 8 is repeated, replacing the chitosan with a myoglobin/oxide mixture. With regard to myoglobin/oxide, see L. Yang et al. *Electrochemistry Communications* 9 (2007) 1057-1061).

EXAMPLE 10

Stents are first provided with a phytate conversion layer as in Example 1. Then the stents are coated in a layer-by-layer process. First, the stents are dipped in a solution of chitosan (e.g., 0.2 wt %, pH 5, which may be prepared in accordance with the procedures of G. Zhao et al., *Electrochemistry Communications* 8 (2006) 148-154). Then the stents are dipped in a solution of a hyaluronic acid-paclitaxel conjugate (e.g., hyaluronic acid-paclitaxel, prepared in accordance with the procedures described in Y. Luo et al., *Biomacromolecules* 1 (2000) 208-218, 1 mg/mL, pH 5). By repeating the dipping procedures in the two different solutions, the multilayer films are formed.

EXAMPLE 11

The procedure of Example 10 is repeated using a hyaluronic acid-everolimus conjugate solution, rather than a hyaluronic acid-paclitaxel conjugate solution.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising a bioerodable metallic region and a bioerodable coating over at least a portion of the metallic region, wherein said coating comprises a multivalent acid comprising multiple phosphoric acid groups, and wherein said coating acts to slow or delay the in vivo degradation of the bioerodable metallic region in vivo.

2. The implantable or insertable medical device of claim 1, wherein the bioerodable metallic region is selected from the group consisting of magnesium, zinc, iron, calcium, alloys that comprise magnesium, alloys that comprise zinc, alloys that comprise iron, and alloys that comprise calcium.

3. The implantable or insertable medical device of claim 1, wherein said multivalent acid is phytic acid.

4. The implantable or insertable medical device of claim 1, wherein said medical device is selected from the group consisting of stents and implantable electrical leads.

5. The implantable or insertable medical device of claim 1, wherein said coating comprises a reaction product of phytic acid and the underlying metallic region.

6. The implantable or insertable medical device of claim 1, wherein said coating further comprises ceramic particles.

7. The implantable or insertable medical device of claim 6, wherein the ceramic particles comprise an oxide selected from the group consisting of oxides of magnesium, calcium, zinc, titanium, iron, aluminum, iridium and silicon.

8. The implantable or insertable medical device of claim 6, further comprising a charged or uncharged therapeutic agent.

9. The implantable or insertable medical device of claim 8, wherein said therapeutic agent is an antirestenotic agent or an angiogenesis inhibitor.

10. The implantable or insertable medical device of claim 6, wherein said coating comprises alternating layers of phytic acid and said ceramic particles.

11. The implantable or insertable medical device of claim 10, comprising at least three layers of phytic acid and at least three layers of said ceramic particles.

12. The implantable or insertable medical device of claim 1, wherein said coating further comprises a charged polymer.

13. The implantable or insertable medical device of claim 12, wherein said charged polymer has a positive net charge.

14. The implantable or insertable medical device of claim 12, wherein said charged polymer comprises a poly(amino acid) sequence.

15. The implantable or insertable medical device of claim 12, wherein said charged polymer promotes endothelialization.

16. The implantable or insertable medical device of claim 12, wherein said coating further comprises ceramic particles.

17. The implantable or insertable medical device of claim 1, wherein the coating thickness ranges between 100 nm and 10,000 nm.

18. The implantable or insertable medical device of claim 1, wherein the coating is a multilayer coating.

19. The implantable or insertable medical device of claim 18, wherein the coating comprises alternating layers of (a) the multivalent acid and (b) a species selected from the group consisting of ceramic particles, metallic particles, particles having a positive net charge, polymers comprising a poly (amino acid) sequence, polymers having a positive net charge, therapeutic agents having a positive net charge.

20. The implantable or insertable medical device of claim 1, wherein the medical device is a stent, wherein the bioerodable metallic region is selected from the group consisting of magnesium, zinc, iron, calcium, alloys that comprise magnesium, alloys that comprise zinc, alloys that comprise iron, and alloys that comprise calcium, wherein the coating comprises alternating layers of phytic acid and ceramic particles and wherein the coating comprises an outer layer comprising a polymer that comprises poly(amino acid) sequence that promotes endothelial cell adhesion.

21. The implantable or insertable medical device of claim 20, wherein said coating further comprises an antirestenotic agent or an angiogenesis inhibitor.

22. The implantable or insertable medical device of claim 1, wherein the medical device comprises a biostable metallic substrate that comprises a first depression, wherein the first depression is at least partially filled with a first composition comprising a first therapeutic agent, wherein the bioerodable metallic region is a first bioerodable metallic layer that is disposed over the first composition, and wherein said coating is disposed over the first bioerodable metallic layer.

23. The implantable or insertable medical device of claim 22, wherein the metallic substrate further comprises a second depression, wherein the second depression is at least partially filled with a second composition comprising a second therapeutic agent that may be the same or different from the first therapeutic agent, wherein a second bioerodable metallic layer is disposed over the second composition, wherein the second bioerodable metallic layer differs from the first bioerodable metallic layer in thickness, in composition or both, and wherein said coating is disposed over the first and second bioerodable metallic layers.

24. The implantable or insertable medical device of claim 19 wherein said coating comprises at least three layers of said multivalent acid.

25. The implantable or insertable medical device of claim 24, wherein the bioerodable metallic region is selected from the group consisting of magnesium and magnesium alloys.

26. The implantable or insertable medical device of claim 25, wherein said coating comprises a reaction product of phytic acid and the underlying metallic region.

27. The implantable or insertable medical device of claim 5, wherein the bioerodable metallic region is selected from the group consisting of magnesium and magnesium alloys.

* * * * *

UNITED STATES PATENT AND TRADEMARK OFFICE
CERTIFICATE OF CORRECTION

PATENT NO.        : 8,277,833 B2
APPLICATION NO.   : 12/489996
DATED             : October 2, 2012
INVENTOR(S)       : Liliana Atanasoska et al.

It is certified that error appears in the above-identified patent and that said Letters Patent is hereby corrected as shown below:

Col. 16, line 44, after "20mM $FeCl_3$" change "($FeC;_3 \cdot 6H_2O$," to --($FeCl_3 \cdot 6H_2O$,--.

Signed and Sealed this
Twelfth Day of February, 2013

Teresa Stanek Rea
*Acting Director of the United States Patent and Trademark Office*